United States Patent
Hlavac

(10) Patent No.: US 6,886,276 B2
(45) Date of Patent: May 3, 2005

(54) PLANTAR FASCIA SUPPORT APPARATUS

(76) Inventor: Harry H. Hlavac, 49 Eucalyptus Knoll, Mill Valley, CA (US) 94941-4643

( * ) Notice: Subject to any disclaimer, the term of this patent is extended or adjusted under 35 U.S.C. 154(b) by 31 days.

(21) Appl. No.: 10/326,357

(22) Filed: Dec. 20, 2002

(65) Prior Publication Data
US 2004/0118020 A1 Jun. 24, 2004

(51) Int. Cl.$^7$ ................................................. A43B 7/18
(52) U.S. Cl. .............................. 36/166; 36/170; 36/173; 36/174; 2/240; 602/66
(58) Field of Search .................... 36/140, 145, 166, 36/170, 173, 174; 2/239, 240; 602/63, 66

(56) References Cited

U.S. PATENT DOCUMENTS

| | | | |
|---|---|---|---|
| 366,590 A | 7/1887 | Lubin | |
| 822,138 A | * 5/1906 | Little | .......................... 602/66 |
| 1,220,724 A | * 3/1917 | Burns | .......................... 36/166 |
| 1,395,512 A | 11/1921 | Murphy | |
| 1,565,259 A | * 12/1925 | Collis | .......................... 602/66 |
| 1,727,586 A | * 9/1929 | Condon | ............................ 2/61 |
| 1,731,216 A | 10/1929 | Peacock | |
| 2,106,430 A | 1/1938 | Humblet | |
| 2,774,322 A | 12/1956 | Harris | |
| 4,064,566 A | 12/1977 | Fletcher et al. | |
| 4,085,745 A | 4/1978 | Alenares | |
| 4,461,288 A | 7/1984 | Curtis | |
| 4,476,858 A | 10/1984 | Curtis | |
| 4,649,939 A | 3/1987 | Curtis | |
| 5,092,318 A | 3/1992 | More et al. | |

* cited by examiner

*Primary Examiner*—Ted Kavanaugh
(74) *Attorney, Agent, or Firm*—Dergosits & Noah LLP

(57) ABSTRACT

A support apparatus for supporting the plantar fascia of a foot. The support apparatus is made of an elastic material expandable in the width and longitudinal axis of the foot. When in operative position on the foot, the apparatus frictionally remains in place mid the first metatarsal bone and extends behind the heel of the foot above its os calcis bone such that when the foot is caused to bear weight, the apparatus expands along the longitudinal axis of the foot to its limit of expandability such that the arch of the foot is maintained substantially unchanged as the foot alternates between load bearing and non-load bearing orientations.

12 Claims, 5 Drawing Sheets

PLANTAR FASCIA SUPPORT APPARATUS

FIELD OF THE INVENTION

The present invention relates generally to the field of support devices for protecting anatomical parts; more particularly to an apparatus for supporting and stabilizing the plantar fascia of the foot, and a method for integrating this support with the sole of a shoe.

BACKGROUND OF THE INVENTION

The human foot is commonly subjected to strong forces even during ordinary daily activity. Athletes frequently subject their feet to particularly severe shock forces and shearing forces during intense physical activity such as jumping. As a result, a variety of injuries to the foot are sustained by athletes. In addition, chronic conditions may develop as a result of continual stressing of the foot. These conditions produce the overuse syndrome, caused by impact shock, hypermobility, and imbalance. One such condition is known as plantar fascists.

The plantar fascia is a tough fibrous band within the foot that extends from the bottom of the heel bone to each of the toes. The bottom or plantar structures of the foot are supported by bones, muscles, ligaments and inelastic connective tissue called "fascia."

The plantar fascia serves several important functions. First, it prevents the foot from over-spreading while the foot is supporting the body weight. Second, it provides a springing force during push-off of the foot during motion, for example jumping. It is therefore important that the plantar fascia remain rigid enough to maintain the foot in an unspread position while maintaining sufficient elasticity to provide the desired springing force. Third, the plantar fascia prevents the arch structures from collapsing, and fourth, provides stability of the forefoot on the rearfoot against supporting surfaces during the lift-off phase of gait. Once stabilized against the ground during gait, as the heel lifts and as the toes roll up, the windlass action of the normal plantar fascia, in conjunction with the calf muscle, will lift, pull forward, and invert (resupinate) the heel bone restoring the medial longitudinal arch. Fifth, the plantar fascia acts as a bowstring that maintains flexibility under tension by anchoring the support structures at both ends of the arch. The plantar fascia is the retaining cable of the longitudinal arch. The plantar fascia assists in resupination of the subtalar joint during the propulsive phase of walking gait. The plantar fascia assists the deep posterior muscles by helping to limit subtalar joint pronation during standing and walking. The plantar fascia is under the greatest tension just before the heel lifts off the ground. Sixth, the plantar fascia acts to store energy within the arch structure of the foot during dynamic loading, standing, walking, running. Therefore, the plantar fascia acts like a spring under the arch of the foot to first absorb energy during weight-bearing and restore the relaxed position as the arch rises.

If a sufficient impact, strain or pressure is exerted upon the bottom of the foot, the plantar fascia may over-stretch or develop micro-tears, tears at its attachment from tension pulling on the heel bone as the foot moves upwards at the ankle joint. This condition is known as plantar fasciistis. Plantar fasciistis seldom develops as the result of a single traumatic occurrence or injury, but rather develops slowly as the result of activities which place recurring stress upon the plantar fascia. For example, wearing shoes which lack adequate arch support for the foot or shank support within the shoe can provide such stress, particularly for individuals with the extremes of hypermobile flat feet or rigid high arched feet. Also, shoes with very stiff soles may require exertion of additional force to flex under the ball of the foot. In addition, increased stress on the plantar fascia due to increased weight or high-impact sports may result in plantar fasciistis.

Plantar fasciitis leads to pain on weight-bearing and tenderness to deep pressure over the plantar fascia at the heel-bone junction. Swelling and inflammation may develop. These conditions worsen with activity. Any activity which causes the foot to spread, such as prolonged standing, or which causes springing of the foot such as running and jumping will aggravate the condition.

Plantar fasciitis is also commonly known as the "heel spur syndrome." This name arose because as the plantar fascia is under prolonged or increased tension, it becomes excessively stretched for prolonged periods and the point of attachment of the plantar fascia to the heel may become calcified leading to bone growth that is often times referred to as a heel spur. In severe cases of plantar fasciitis, surgery is performed to permanently separate the plantar fascia from the heel spur. This surgery requires months for recovery. The separation of the plantar fascia from the heel results in a collapsed arch, as the plantar fascia is no longer capable of providing support. Surgery therefore results in the need for the permanent use of custom orthotics-arch supports for the foot to be worn within shoes to provide support for the foot. Finally, the plantar fascia is also unable to assist in springing, resulting in diminished locomotion and inability to push off the planted foot.

Early treatment is therefore essential in maintaining long-term active use of the foot. Treatment is focused upon reduction of stress to the foot which would cause the foot to spread. This commonly involves resting the foot or the use of custom orthotics devices. Unfortunately, these orthotics cannot fully support the arch of the foot except while the foot is flat against the ground or other hard surface, as there is no attachment of the orthotic to the foot. The orthotic cannot provide full support to the arch during the critical periods of motion during which the foot is landing or springing forward. Custom made foot arch supports, commercial arch supports, and functional foot orthotic devices support the arch and cup the heel but do not prevent elongation of the foot upon contact or push-off during gait.

Many devices which provide some measure of support to structures of the foot are ineffective in providing support for the plantar fascia. One such device is taught by Alenares, U.S. Pat. No. 4,085,745. Alenares teaches a foot support constructed from a two-way stretch material which provides uniform pressure across the surface of the foot to support the venous system of the foot. Such a support is too elastic in the direction parallel to the length of the foot, hereinafter referred to as the long axis of the foot, to maintain the arch of the foot in a rigid configuration necessary to support the plantar fascia. Ordinary two-way stretch material will not provide such support as long as the material retains equal elasticity in all directions, as rigidity is desired in the direction of the long axis, while some flexibility is desired in the direction perpendicular to the long axis in order to facilitate motion of the foot.

One method successfully used to treat plantar fasciitis is to tape the foot into a resting position in a manner to provide support to the foot. One such method is known as the Low-Dye strap method of taping. In a variation of this method adhesive tape is applied from the arch on the outside of the foot around and under the heel of the foot, wrapping forward and extending to the inner arch of the foot to a point forward of the midfoot. Finally, strips are wrapped about the foot from the instep to the bottom of the foot, encircling the front portion of the foot midshaft of the first metatarsal bone, between the first metatarsal-first cuneiform joint and the first phalangeal-metatarsal joint, which is the joint of the big toe to the foot.

This method provides several advantages. The arch is supported by anchoring points at both ends of the arch, thereby providing mechanical support. This prevents the arch from collapsing and from the foot elongating. The foot is held in a semi-rigid manner, thereby both preventing over-spreading of the foot as well as allowing springing during toe-off by holding the bones and joints of the foot in proper alignment.

Unfortunately, this method has several significant disadvantages. The method requires that the tape be applied on a regular basis. This results in the wearer being required to perform the time consuming task of applying the tape. Many individuals may feel uncomfortable with applying the taping themselves. Thus the difficulty of the procedure discourages use of the method by many individuals who would benefit from its effects.

In addition, the tapes lose their effectiveness if adhesion to the skin is diminished. As a result, taping is ineffective if the foot becomes wet. If the tape becomes wet or disattaches, retaping becomes necessary. The need for retaping may arise under circumstances which are not conducive to the lengthy retaping process, as the wearer will commonly be engaged in some sort of physical activity at the time.

Also, many individuals suffer allergic reactions to the adhesive in the tape. Long term continuous use of adhesive tape on the body may be harmful to the skin. The difficulty in applying the tape may lead to individuals choosing to wear the tape for long periods rather than retaping.

Therefore, there is clearly a strong need for a support apparatus for the foot which provides support to the plantar fascia and the arch of the foot without requiring difficult and time consuming taping procedures or expensive custom made foot orthoses.

Generally, it is an object of the present invention to provide an improved method and support apparatus for the plantar fascia of the foot.

Another object of the present invention is to provide a support apparatus for the plantar fascia of the foot which may be easily placed in operative position on the foot and designed to be used interchangeably on the right or left foot, or inside—out. Other objects of the present invention will become apparent to those skilled in the art from the following description and accompanying claims and drawings.

SUMMARY OF THE INVENTION

Very generally, the present invention comprises a support apparatus for supporting the plantar fascia of the foot. The support apparatus includes a first portion which is secured by tension mid shaft of the first metatarsal bone, between the joints with the first phalangeal (great toe) bone and the first cuneiform bone, when in operative position on the foot. The support apparatus also includes a second portion which extends from said first portion around and behind the heel of the foot when in operative position. The second portion is sufficiently inelastic in the direction parallel to the axis of the foot that the arch of the foot is maintained in a substantially relaxed non-weightbearing position.

In the preferred embodiment of the present invention, the second portion is manufactured from a two way stretch elastic material shaped such that said second portion is fully stretched in the direction parallel to the axis of the foot when in operative position on the weight-bearing foot. In a variation of this apparatus, the front bottom first portion of the support may extend to attach to the sole of the shoe. When bearing weight, the extension is under the ball of the foot similar to the plantar fascia itself which then pulls the heel forward as the toes rise. In particular, the preferred two way stretch elastic cushioned material used is neoprene. This type of material dissipates shock on heel contact, delays expansion of the foot on forefoot contact, prevents collapse of the arch with weightbearing, and restores the relaxed position to the foot as the heel leaves the ground during forward motion.

In combination with a dynamic sole design, the plantar fascia support apparatus assists the forward movement of the body weight over the weight-bearing foot.

DETAILED DESCRIPTION OF THE INVENTION

Figure 1:
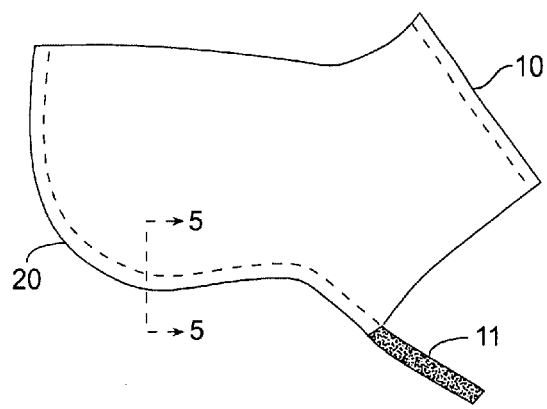
FIG. 1 a plan side view of one embodiment of the present invention.
Figure 1A:
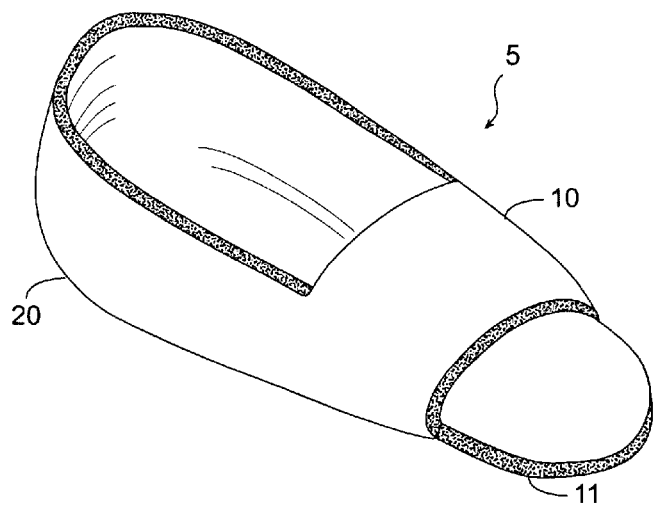
FIG. 1A is a perspective drawing of the embodiment of FIG. 1.

The preferred embodiment of the support apparatus of the present invention is illustrated by side view in FIG. 1 and in perspective view in FIG. 1A.

Figure 4:
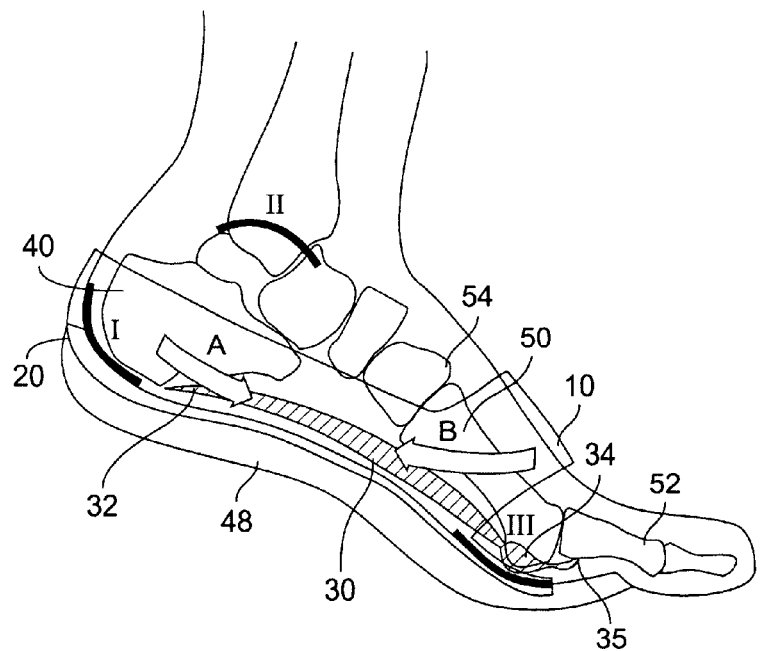
FIG. 4 is a side plan view of one embodiment of the present invention in operative position on a foot which is in a toe-off state with the underlying structure of the foot.

The support apparatus comprises two major portions. The first portion 10 is essentially tubular in shape. The second portion 20 is shaped like the heel of the foot, and may be attached to first portion 10 to form a unitary piece. Support apparatus 5 may be constructed (molded) as a single sheet or sewn to form the unitary piece as shown. Alternatively, a heat seal tape of the same or similar material may be utilized. Also, support apparatus 5 may be constructed in multiple pieces. As a preferred embodiment, bottom front portion 11 of apparatus 5 may extend under the weightbearing area of the foot or attach to the top portion of the shoe sole. The plantar fascia support apparatus may be integrated and bonded with the design of the shoe sole to facilitate forward locomotion (FIG. 4).

Figure 2:
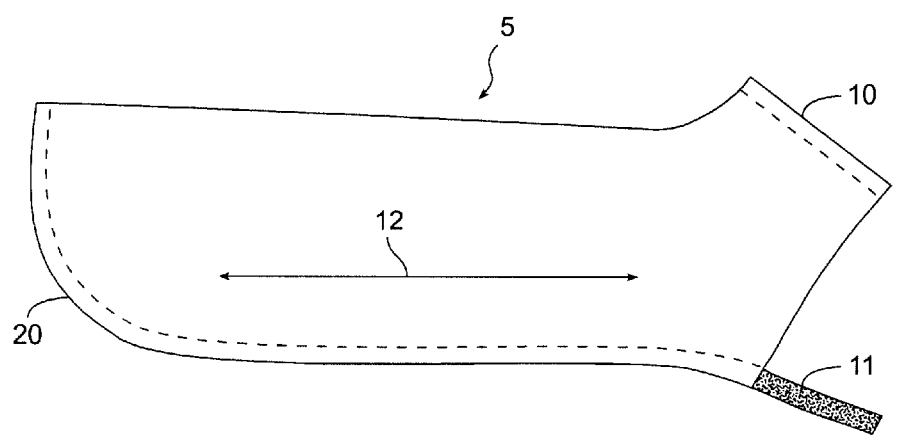
FIG. 2 is a side view of the one embodiment of the present invention in an extended condition, as when in operative position on the foot.
Figure 2A:
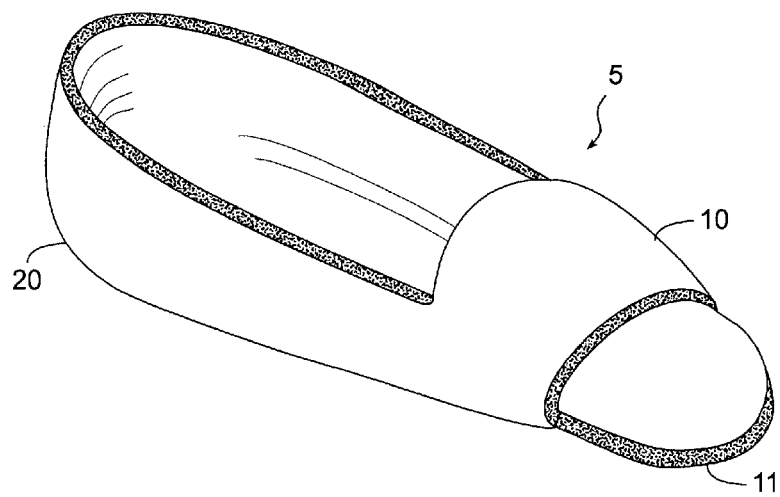
FIG. 2A is a perspective drawing of the embodiment of FIG. 2.

The preferred embodiment of the present invention stretches when worn in operative position on the foot, as illustrated by side view in FIG. 2 and in perspective view in FIG. 2A, with all numbering remaining consistent throughout the figures. Arrow 12 indicates the direction of stretching of the material of support apparatus 5 in the longitudinal direction of the foot. In the preferred embodiment, support apparatus 5 is constructed of a two-way stretch material which is stretched when in position on the foot in the direction of arrow 12 to approximately its limit of expandability. As such, the material becomes effectively a one-way stretch material, with the material resisting stretching in the direction of arrow 12 far more than in the direction perpendicular to arrow 12. The two way stretch feature of this material allows for comfortable individual fit.

Figure 3:
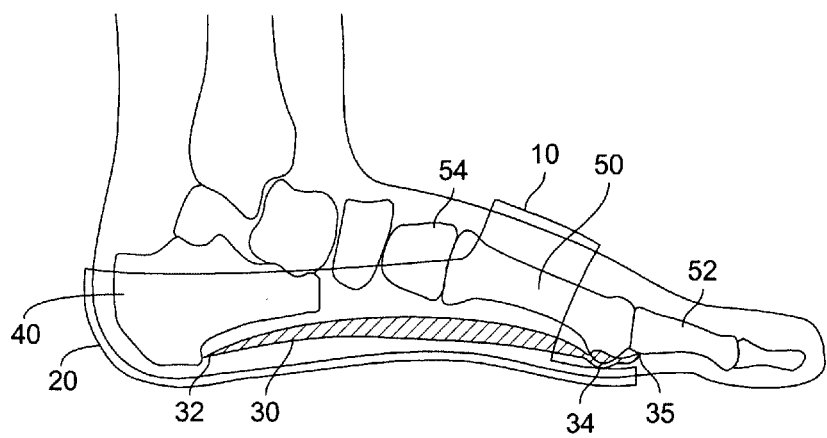
FIG. 3 is a side plan view of one embodiment of the present invention in operative position on a foot which is at rest in a weight-bearing state with the underlying bone structure of the foot.

The operation of support apparatus 5 may now be explained in view of the operation of the foot. FIG. 3 illustrates the preferred embodiment of the present invention in operative position on a foot which is at rest in a weight-bearing state with the underlying bone structure of the foot. First portion 10 encircles the instep of the foot in a location mid shaft of the first metatarsal bone 50. First portion 10 must remain in position in operation between the joints of the first metatarsal bone 50 with the first toe (phalangeal) bone 52 and with the first cuneiform bone 54. If the top and sides of the first portion 10 should extend beyond these joints, proper mechanical operation of the foot is impaired. Therefore first portion 10 must remain in a substantially immovable position on the foot. First portion 10 is maintained in position by mechanical tension caused by the elastic nature of the material comprising the support apparatus. If bottom portion 11 attaches to the sole of the shoe, the pull of the plantar fascia is increased. If the design of the outer sole of the shoe complements the function of the support apparatus as shown in FIG. 4, forward motion is enhanced.

Second portion 20 extends from first portion 10 around and behind the heel of the foot above the middle of the os calcis (heel) bone 40. Second portion 20 is stretched in the direction of the axis of the foot (arrow 12) as shown in FIG. 2. This renders second portion 20 sufficiently inelastic in that direction such that the arch of the foot is maintained fixed in the position ordinarily maintained when the foot is relaxed, i.e. when not bearing weight. This "relaxed" position is therefore maintained even when the arch is subjected to stress. This holds the normal protective fat pad around the heel bone preventing expansion of the heel on contact; also, this prevents over-extension of the plantar fascia 30, which is connected to the os calcis bone 40 at 32 and to the first metatarsal bone at 34 and 35.

Figure 3A:
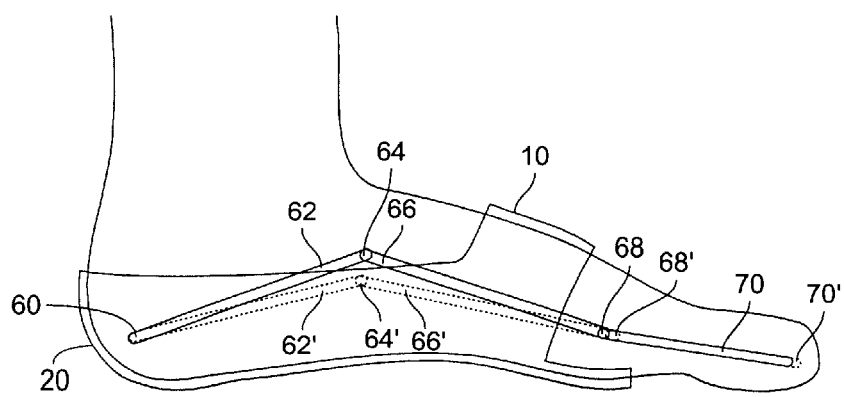
FIG. 3A is a side plan view of the present invention showing the mechanics of the embodiment of FIG. 3.

The manner in which the arch may be maintained in position is best understood in light of FIG. 3A, which is a diagram representing the mechanics of the embodiment of FIG. 3. The bone structure of the foot may be represented as three rigid rods representing the rear arch 62, the forward arch (and instep) 66, and the toes 70. Rear arch 62 and forward arch 66 are connected by a pivot 64, and forward arch 66 and toes 70 are connected by pivot 68. The heel end 60 and pivot 68 respectively correspond to the points of attachment 32 and 34 of plantar fascia 30 to the bone structures of FIG. 3 as well as the sesamoid bone under the ball of the foot which is invested in the plantar fascia and extends to the base of the toes at 35.

Support apparatus 5 operates as follows. First portion 10 is fixed in place on the instep and acts upon forward arch 66. Second portion 20 is fixed in place behind the heel and therefore acts upon heel end 60. Mechanical tension due to elastic forces attempting to restore the material to its unextended state act to place a rearward force upon forward arch 66 and a forward force upon heel end 60. These elastic forces resist motion of the forward arch 66 and heel end 60 away from each other, as the material is inelastic in that direction. These forces act to force heel end 60 and pivot 68 closer, thereby maintaining the arch in shape. Support apparatus 5 is shaped to produce these stabilizing forces when the foot is weight-bearing without unduly forcing the relaxed foot. These dynamic forces are shown in FIG. 4 whereby arrow B indicates the force exerted by first portion 10 proximate the ball of the foot while arrow A represents the force exerted by second portion 20. Together, these dynamic forces act to maintain the arch between the load bearing and non-load bearing orientations of the foot. The present invention prevents foot pad expansion, cushions under the heel bone and restores spring in the arch by preventing expansion and elongation of the fore foot. The extension under the ball of the foot assists the effect of the plantar fascia while the dynamic sole decreases shock on heel impact, lifts under the bottom of the heel, decelerates ankle motion, decreases the amount of dorsiflexion of the foot on the ankle through heel lift and relieves the pressure under the first toe joint and the lesser metatarsals.

FIG. 4 also shows curved bone shapes 1, 2 and 3 known as rockers I, II and III. As background, during the swing phase of walking, the foot hangs in relaxed supination. Just before contact, the foot dorsiflexes at the ankle to clear the ground. At heel contact (rocker I), these dynamics change. Actions are now reactive to impact, to absorb shock and maintain balance. On contact, the heel hits the outside of center with the foot slightly toed out. Immediately thereafter, the shock of impact is dissipated by pronation of the foot to adapt to the supporting surface and to maintain balance noting that this contact phase is also known as the resistance phase.

Upon fore foot contact, the resistance phase ends as stress (center of pressure) passes over rocker II, the ankle/sub-talar complex. On fore foot contact, the rebound force through the mid foot meets the downward force of body weight within the base of support as the center pressure passes through the metatarsal heads (rocker III). As pressure passes the metatarsals, if they are stable, windlass action of the plantar fascia pulls and elevates the heel as the heel leaves the ground entering the lift off phase. By employing the present invention, and particularly its use in conjunction with the appropriate "dynamic" sole, normal foot function is assisted improving cushioning, balance, stability and efficiency.

To compliment rocker I, the contact area 21 located at the heel portion of sole 48 curves and tapers upwardly 20 percent or more as a preferred embodiment. To compliment rocker II at the ankle, sole area 22 of sole 48 located directly under the ankle is preferably at least ¼" thicker than the heel portion of the sole to create a convex outer sole surface. Further, to compliment rocker III under the ball of the foot at 23, the dynamic sole 48 curves upwardly approximately 20 degree as shown. Functionally, this design decreases heel impact, relieving stress on spurs impacting upon the plantar fascia while relieving shock on the Achilles tendon and the ankle joint. Further, as the sole tapers upward under the ball of the foot, there is a smooth rocking motion through the toes, relieving stress through the first toe joint. In combination with the extension of the strap under the ball of the foot, plantar flexure is encountered enhancing resupination through the mid distance into the lift-off phase of gait. This results in a smoother gait making it easier to walk.

When used alone, the plantar fascia support apparatus of the present invention relieves tension on the plantar fascia and prevents elongation and spreading out of the foot, throughout the gait cycle. When used with the plantar extension II attached to the sole, the attachment allows the sole to become part of the enhancement system, pulling on the heel to raise the arch during the lift-off phase of gait. When combined with a dynamic sole (FIG. 4), the foot, sock, shoe system creates a rolling motion where the previous lever action existed. With normal shoes there are two sounds upon walking, that is, heel and fore foot. With the dynamic sole motion enhancement system of the present invention, there is one sound of contact as the foot and shoe more smoothly and quietly move over the supporting surface.

Returning to the appended figures, in the absence of support apparatus 5, the weight of the body over the weight-bearing leg exerts a downward force on rear arch 62. This acts to drive the rear arch downward, illustrated as rear arch 62'. This displacement forces pivot 64 to pivot position 64', and forward arch 66 will shift to forward arch 66'. Finally pivot 68 will move to position pivot 68' and the toes 70 will move forward to toe position 70'. The displacement of pivot 68 to position pivot 68' corresponds to displacement of point of attachment 34 which acts to extend plantar fascia 30. This illustrates that support apparatus 5 acts to substantially prevent over-extension of the plantar fascia during weight-bearing conditions.

Figure 4A:
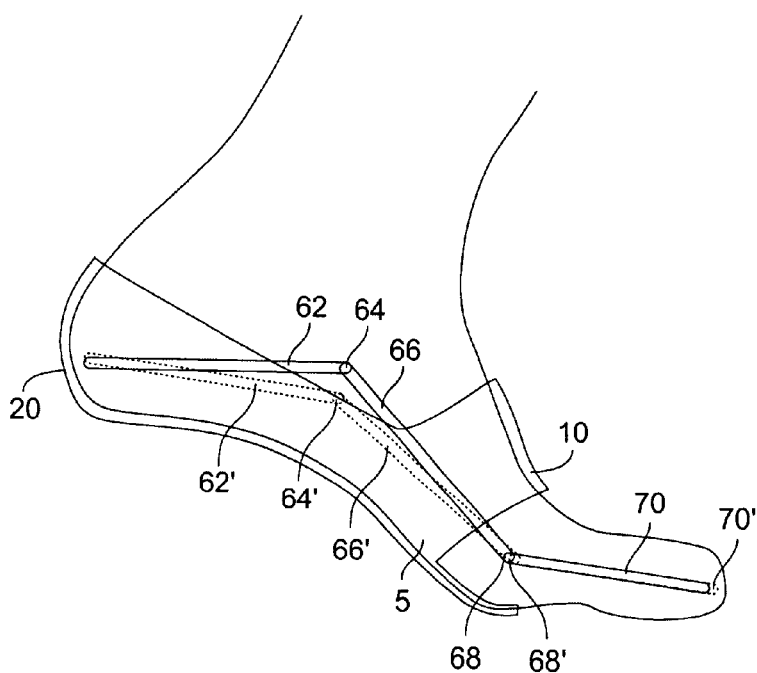
FIG. 4A is a side plan view of the present invention showing the mechanics of the embodiment of FIG. 4.

FIG. 4 illustrates the preferred embodiment of the present invention in which the support apparatus is joined with sole 48 in operative position on a foot which is at rest in a toe-off state with the underlying bone structure of the foot. FIG. 4A is a diagram representing the mechanics of the embodiment of FIG. 4. The operation of support apparatus 5 in these figures is equivalent to those of FIG. 3 and FIG. 3A. It should be noted that the plantar fascia 30 shortens and the arch rises in this position relative to that of FIG. 3 and FIG. 3A.

Figure 5:
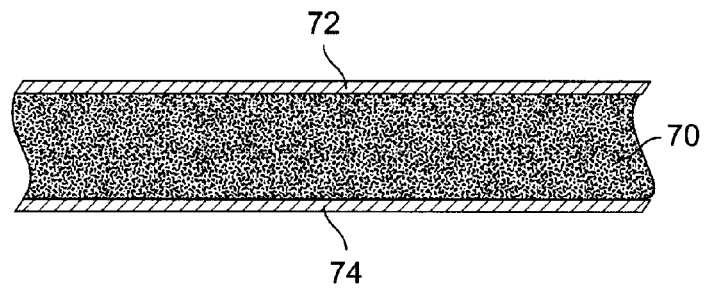
FIG. 5 is a cross-sectioned view of the embodiment of the present invention taken along 5—5 of FIG. 1.

FIG. 5 illustrates a cross-section of the, material of the preferred embodiment of FIG. 1. An elastic material 70 is disposed between an elastic inner fabric 72 and an elastic outer fabric 74. This material should have sufficient thickness of elastic material 70 to cushion the foot upon landing during motion. In the preferred embodiment, the material 70 may be neoprene, although similar materials such as Hypolon™ Fabriform™ may be used. It has been found that ⅛" and 3/16" are suitable thicknesses of these materials.

In considering the present invention, it is important to note that the apparatus disclosed herein supports both ends of the bones of the foot that form the foot's longitudinal arch, that is, the heel bone and the metatarsal bones. As such, the effect of force applied to the foot (arrows A and B of FIG. 4) in employing the present apparatus creates an effective force in front of (anterior II) the middle of the metatarsals which then form a truss support. Further, second portion 20 of the present invention appends to the lower portion of the heel bone resulting in elastic compression of the normally protective fat pad around the heel. By holding the fat pad under the weight-bearing area of the foot provides cushioning to the bottom of the heel. Finally, in positioning the first portion 10 as described, frictional compression is applied over the front of the metatarsal bones of the foot and not over the transverse arch. This allows and, in fact, indirectly assists in the normal motion of the foot at the transverse tarsal arch.

Figure 7:
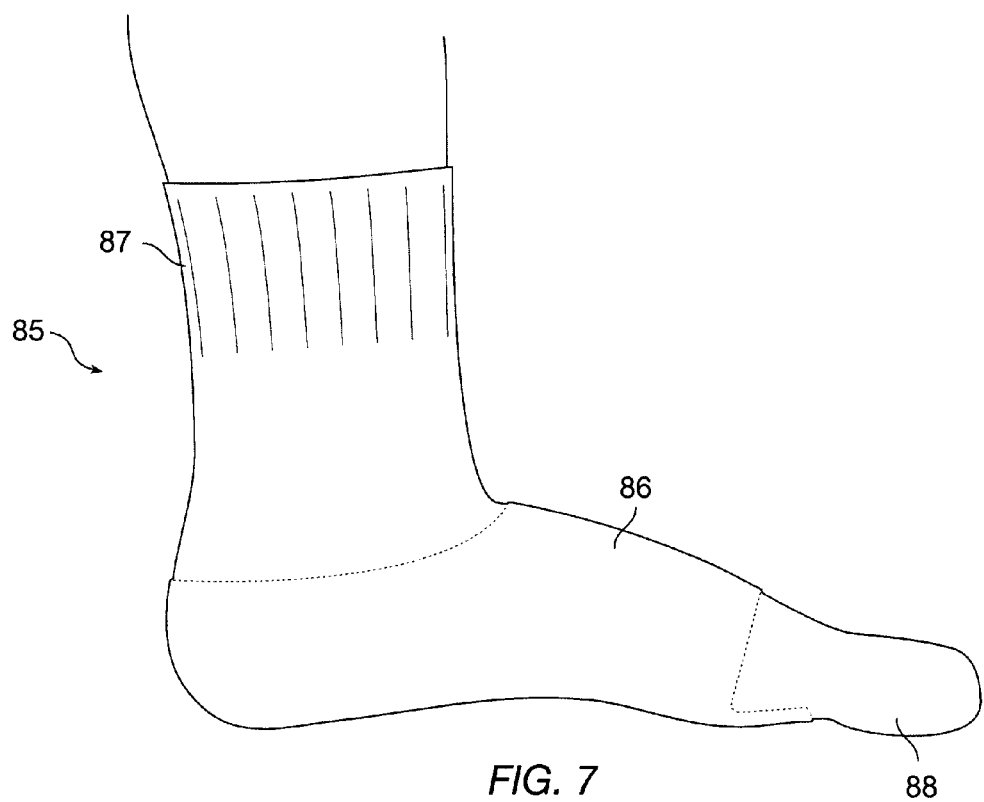
FIG. 7 is a side plan view of the invention configured as being part of a stocking or hose.

As noted previously, although a cushioning material having elastic properties such as neoprene can be employed in practicing the present invention, a fine stocking or hose could likewise be employed as long as the frictional fit and elasticity as described and claimed herein characterized such an apparatus. As such, reference is made to FIG. 7, showing stocking 85. In this embodiment, the stocking can be constructed as a unitary piece with section 86 operating as apparatus 5 discussed previously. In doing so, calf and toe regions 87 and 88 respectively need not possess any compressive properties but could instead replicate ordinary hose, or support hose, of the prior art. This embodiment would be more useful in its application in a dress environment rather than in the normally casual environment conducive to the use of a neoprene apparatus.

Figure 6:
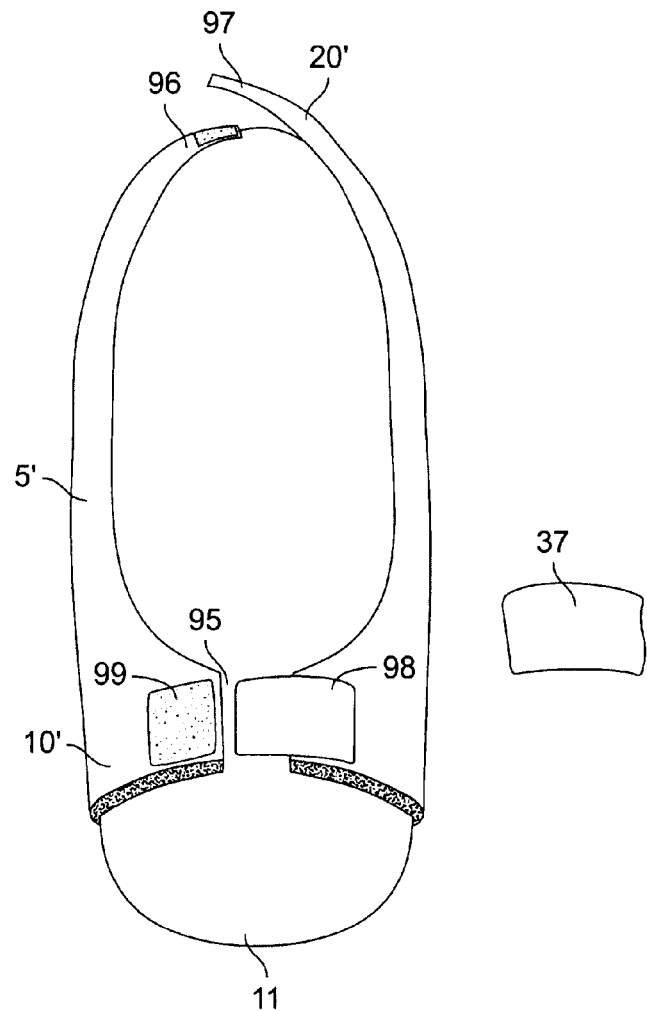
FIG. 6 shows, in top plan view, a preferred embodiment of the invention wherein the invention is depicted as being adjustable.

In addition, the present apparatus can be made adjustable. In this regard, reference is made to FIG. 6 which shows such feature. Specifically apparatus 5' is configured with open or detached region 95 within first portion 10' and 96 within second portion 20'. Connecting pad 37 can be employed to adjustably join ends 98 and 99 by Velcro™ or similar attachment means. Similarly, flap 97 can be adjustably joined to second portion 20' to adjust the apparatus to feet of varying sizes.

Various modifications of the invention in addition to those shown and described herein will become apparent to those skilled in the art from the foregoing description and accompanying drawings. Such modifications are intended to fall within the scope of the appended claims.

What is claimed is:

1. A support apparatus for supporting the plantar fascia of a foot, said foot having an arch, a width and a longitudinal axis extending from the toes to the heel of the foot perpendicular to said width, said support apparatus being comprised of an elastic material expandable in said width and longitudinal axis directions and having a limit of expandability beyond which substantially no further expansion is possible, said support apparatus comprising a first portion and a second portion, said first portion, when in operative position on the foot expands to frictionally encircle the instep of the foot and remain in place during walking between the joints of the first metatarsal bone and phalangeal bone and first metatarsal bone and cuneiform bone and joined to the second portion, said second portion extending from said first portion around and behind the heel of the foot above its os calcis bone such that when said foot is caused to bear the weight of a user, said second portion expands along said longitudinal axis to approximately its limit of expandability such that said arch is maintained substantially unchanged as said foot alternates between load bearing and non-load bearing orientations.

2. The support apparatus of claim 1 wherein said support apparatus is comprised of neoprene.

3. The support apparatus of claim 1 wherein said first portion and said second portion are configured such that said support apparatus is interchangeably operative on both right and left feet.

4. The support apparatus of claim 1 wherein said first portion and said second portion are configured such that said support apparatus can be employed inside out.

5. The support apparatus of claim 1 wherein said first portion and said second portion are integrally joined to a stocking.

6. The support apparatus of claim 5 wherein said stocking comprises a compression stocking.

7. The support apparatus of claim 1 wherein said support apparatus is attachable to a sole of a shoe.

8. The support apparatus of claim 7 wherein an extension is provided for attaching said support apparatus to said sole of said shoe proximate the ball of the foot when said support apparatus is being worn by a user.

9. The support apparatus of claim 7 wherein said sole tapers upwardly proximate to its heel portion.

10. The support apparatus of claim 7 wherein said sole tapers upwardly proximate the ball of the foot.

11. The support apparatus of claim 7 wherein said sole is thicker under the ankle portion of the foot as compared to the heel portion.

12. The support apparatus of claim 1 wherein said first portion and said second portion are adjustable to accommodate feet of varying sizes.

* * * * *